United States Patent [19]

Parkinson et al.

[11] Patent Number: 5,750,734
[45] Date of Patent: May 12, 1998

[54] PROCESS FOR THE PREPARATION OF STEROID DERIVATIVES

[75] Inventors: Nigel Christopher Parkinson; Andrew Paul Van Sickle, both of Dagenham, United Kingdom

[73] Assignee: Rhone-Poulenc Rorer Limited, West Malling, England

[21] Appl. No.: 849,015

[22] PCT Filed: Nov. 2, 1995

[86] PCT No.: PCT/GB95/02568

§ 371 Date: May 23, 1997

§ 102(e) Date: May 23, 1997

[87] PCT Pub. No.: WO96/16978

PCT Pub. Date: Jun. 6, 1996

[30] Foreign Application Priority Data

Nov. 26, 1994 [GB] United Kingdom ............. 9423919

[51] Int. Cl.$^6$ ............................................. C07J 71/00
[52] U.S. Cl. ............................................. 549/432
[58] Field of Search ............................................. 549/432

[56] References Cited

U.S. PATENT DOCUMENTS 4,221,786  9/1980  Kalvoda ........................... 549/432

FOREIGN PATENT DOCUMENTS

| 0 164 636 | 12/1985 | European Pat. Off. . |
| 0164636 | 12/1985 | European Pat. Off. . |
| 0 197 018 | 10/1986 | European Pat. Off. . |
| 0 262 108 | 3/1988 | European Pat. Off. . |
| 0 355 859 | 2/1990 | European Pat. Off. . |
| 0 508 900 | 10/1992 | European Pat. Off. . |
| 2185405 | 1/1974 | France . |
| 1118779 | 12/1961 | Germany . |
| 527509A1 | 11/1983 | Spain . |
| 92/13872 | 8/1992 | WIPO . |
| 9213872 | 8/1992 | WIPO . |

*Primary Examiner*—Mukund J. Shah
*Assistant Examiner*—King Lit Wong
*Attorney, Agent, or Firm*—Ross J. Oehler, Esq.

[57] ABSTRACT

A process is described for the preparation of a compound of formula (I) or a stereoisomeric compound thereof, in which the 1,2-position is saturated or is a double bond; $X^1$ and $X^2$ are each independently hydrogen or halogen; $R^1$ is hydrogen or acyl; $R^2$ is hydroxyl, acyloxy or oxo; and $R^3$ is alkyl, by reacting a compound of formula (II) with an aldehyde $R^3CHO$ in either phosphoric acid or about 60% to about 75% w/w sulphuric acid. Compounds of formula (I) are either pharmacologically active steroids or are intermediates in the synthesis of pharmacologically active steroids.

27 Claims, No Drawings

PROCESS FOR THE PREPARATION OF STEROID DERIVATIVES

This is a 371 application of PCT/GB95/02568, filed Nov. 2, 1995.

The present invention relates an improved process for the preparation of 16,17-acetals of pregnane derivatives by the transacetalisation of the corresponding 16,17-acetonides. The process of the invention is conveniently applicable to the synthesis of intermediates useful for the preparation of pharmacologically active steroids, such as compounds described, for example, in WO 94/14834. The present process also directly provides known pharmacologically active steroids such as budesonide.

Methods for the preparation of 16,17-acetals of pregnane derivatives, which are based upon the transacetalisation of 16,17-acetonides with an aldehyde, are described in EP-B-355859, EP-B-262108, EP-A2-164636 and ES527509A1. Each of the methods therein describes the transacetalisation either in a heterogeneous system comprising an organic solvent and a catalytic amount of perchloric acid or a hydrohalogen or organic sulphonic acid, or in a homogeneous system where the aqueous hydrohalogen (e.g. hydrofluoric or hydrochloric) acid is also the solvent for the reaction. However, none of the aforementioned methods are ideal for various reasons. The use of hydrofluoric or hydrochloric acid on a large scale requires specialised equipment, and reaction with hydrofluoric acid at low temperatures (as described in EP-A2-164636) is especially difficult to apply industrially. Heterogeneous systems involve the use of high dilution and/or abrasive distribution modifiers with an oxidising acid to achieve a good epimeric distribution at C22.

The present invention overcomes the drawbacks in the art methodology by utilising sulphuric acid or phosphoric acid as a reactive solvent. Thus, according to a first aspect, the invention provides a process for the preparation of a compound of formula (I)

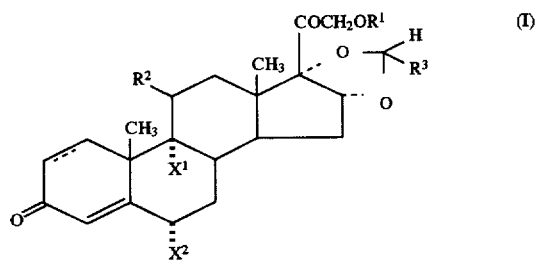

or a stereoisomeric compound thereof, wherein:

the 1,2-position is saturated or is a double bond; $X^1$ and $X^2$ are each independently hydrogen or halogen;

$R^1$ is hydrogen or acyl;

$R^2$ is hydroxyl, acyloxy or oxo; and $R^3$ is alkyl, comprising
reacting a compound of formula (II)

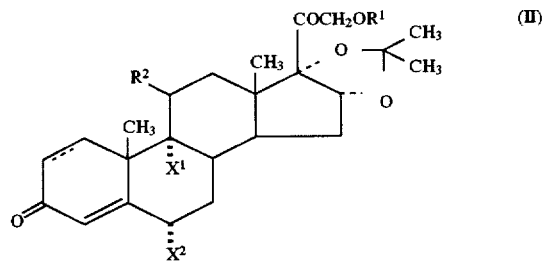

(wherein the 1,2-position is saturated or is a double bond and $X^1$, $X^2$, $R^1$ and $R^2$ are as defined hereinabove) with an aldehyde $R^3$CHO (wherein $R^3$ is as defined hereinabove) in either phosphoric acid or about 60% to about 75% w/w sulphuric acid. The reaction may conveniently be effected at a temperature within the range of about 0° C. to about 50° C., and preferably at about 20° C.

As herein described, the term "halogen" means fluorine, chlorine, bromine or iodine and is preferably fluorine. The term "acyl" as a group or part of an "acyloxy" group includes, for example, a group with 1–10 carbon atoms arranged in a straight or branched chain and is preferably a $C_{2-6}$alkanoyl group (e.g. acetyl). The term "alkyl" within $R^3$ includes a straight or branched hydrocarbon chain having 1–10 carbon atoms and is preferably a $C_{1-4}$alkyl group, especially n-propyl.

The process of the present invention has a number of advantages over the methods in the art. Thus, for example, sulphuric acid and phosphoric acid are inexpensive reagents which are non-oxidising and can be used on an industrial scale without specialised equipment. The use of sulphuric acid or phosphoric acid as the solvent for the reaction means that the reaction is homogeneous and is consequently facile and scalable. The reaction also proceeds in high epimeric distribution, i.e. with a high propensity for (R) stereochemistry at $C_{22}$.

The process of the present invention may preferably be used to prepare compounds of formula (I) in which $R^1$ is hydrogen and $R^2$ is hydroxyl.

The process of the present invention may also preferably be used to prepare compounds of formula (I) in which $X^1$ and $X^2$ are both fluorine atoms.

The present process is particularly suitable for the preparation of a compound of formula (III)

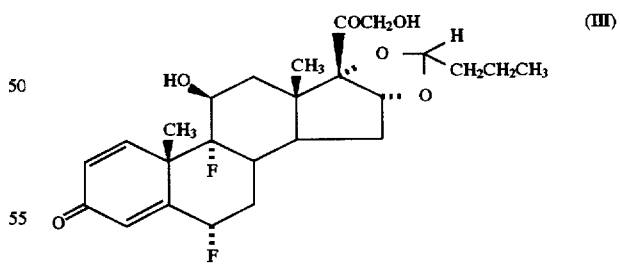

or a stereoisomeric compound thereof, especially the 22R-isomer thereof (i.e. the compound (22R)-16α,17α-butylidenedioxy-6α,9α-difluoro-11β,21-dihydroxypregna-1,4-diene-3,20-dione), from fluocinolone acetonide.

In one particular embodiment of the present invention, the transacetalisation may conveniently be effected using about 60% to about 75% w/w sulphuric acid, preferably using about 60% to about 70% w/w sulphuric acid, especially about 60% to about 65% w/w sulphuric acid.

In another particular embodiment of the present invention, the transacetalisation may conveniently be effected using phosphoric acid, preferably using commercial (i.e. about 85% w/w) phosphoric acid.

The process of the present invention proceeds to provide a high R/S ratio of products. The percentage of 22R-isomer in the product may however be further increased by treating a compound of formula (I) prepared by the process of the present invention with a catalytic amount of perchloric acid in a suitable solvent such as a halogenated hydrocarbon solvent, e.g. dichloromethane.

The process comprising treating a compound of formula (II) as defined hereinabove with an aldehyde $R^3CHO$ as defined hereinabove in either phosphoric acid or sulphuric acid under the conditions described hereinabove, followed by treatment of the resulting compound of formula (I) as defined hereinabove with a catalytic amount of perchloric acid in a suitable solvent such as a halogenated hydrocarbon solvent (e.g. dichloromethane) represents a further aspect of the present invention.

Intermediate compounds of formula (II) are known compounds and may be prepared according to methods reported in the art, for example, as described in EP-B-355859, EP-B-262108, EP-A2-164636 and ES527509A1, or according to methods similar to those described therein.

Compounds of formula (I) in which $R^2$ is oxo and their stereoisomers are novel compounds and represent a further aspect of the present invention.

The process of the present invention is illustrated in the following Examples which are not intended to limit the invention in any way. In the following Examples HPLC means high performance liquid chromatography.

EXAMPLE 1

(22R) -16α,17α-Butylidenedioxy-6α,9α-difluoro-11β,21-dihydroxypregna-1,4-diene-3,20-dione (a) To a 3-necked 3 Liter flask was charged fluocinolone acetonide (100.00 g) and 60% w/w sulphuric acid (1000 mL). The suspension was stirred for 5 minutes and butanal added in one portion (22 mL). The solution was then stirred for approximately 3 hrs. Dichloromethane (500 mL) was then added and the biphasic solution stirred for 5 minutes before addition of a further 250 mL demineralised water. The biphasic solution was stirred for 20 minutes before separation of the aqueous layer, which was discarded. Examination of the dichloromethane layer by HPLC indicated complete reaction with the formation of the title compound (by comparison with an authentic sample) mixed with about 13% of the 22S-epimer.

(b) To further increase the R/S ratio, the dichloromethane solution of the product of part (a) was diluted with 1500 mL of dichloromethane and 70% perchloric acid (75 mL) added in one portion. The thick suspension was then stirred for approximately 18 hrs. To the reaction flask was added demineralised water (200 mL) and the mixture stirred for a further 10 minutes. The organic layer was separated and washed with 10% w/v potassium carbonate solution (250 mL), then with 200 mL of demineralised water to provide the title compound mixed with the 22S-isomer in which the R/S ratio was determined by HPLC at about 10:1.

EXAMPLE 2

(22R)-16α,17α-Butylidenedioxy-6α,9α-difluoro-11β,21-dihydroxypregna-1,4-diene-3,20-dione Fluocinolone acetonide (10.00 g) was dissolved with vigorous stirring and warming in 85% phosphoric acid (75 mL). The solution was cooled to room temperature and butanal (2.0 mL) was added dropwise over 5 min. The solution was stirred a further 4 h at room temperature and was then poured onto 150 g crushed ice. The product was extracted with dichloromethane. The organic solution was washed successively with 10% aqueous sodium carbonate, water and aqueous sodium chloride solutions, dried over magnesium sulphate and concentrated under reduced pressure to leave the title compound as a glassy foam (9.24 g). The product was confirmed as a mixture of diastereomers with a R:S ratio at C22 of approximately 7/1 by HPLC and NMR comparison with an authentic sample.

EXAMPLE 3

(22R)-16α,17α-Butylidenedioxy-6α,9α-difluoro-11β,21-dihydroxypregna-1,4-diene-3,20-dione Fluocinolone acetonide (5.00 g) was added to a stirred solution of 64% w/w sulphuric acid (50 ml). After stirring for 5 minutes butanal (1.1 mL) was added and the mixture stirred at 25° C. for 3 hours.

To the solution was added dichloromethane (25 ml) and then water (27 ml). The organic layer was washed with 10 % w/v potassium carbonate (25 ml) and finally water (25 ml). The organic layer was dried with magnesium sulphate and evaporated to dryness to give the title compound as a light brown solid (5.1 g). The product was confirmed as a mixture of diastereomers containing 87% R isomer by HPLC and NMR comparison with an authentic sample.

EXAMPLE 4

(22R)-16α,17α-Butylidenedioxy-6α,9α-difluoro-11β,21-dihydroxypregna-1,4-diene-3,20-dione Fluocinolone acetonide (5.00 g) was added to a stirred solution of 70%w/w sulphuric acid (50 ml). After stirring for 5 minutes butanal (1.1 mL) was added and the mixture stirred at 25° C. for 2 hours. To the solution was added dichloromethane (25 ml) and then water (27 ml). The organic layer was washed with 10% w/v potassium carbonate (25 ml) and finally water (25 ml). The organic layer was dried with magnesium sulphate and evaporated to dryness to give the title compound as a light brown solid (5.87 g). The product was confirmed as a mixture of diastereomers containing 87.6% R isomer by HPLC and NMR comparison with an authentic sample.

We claim:

1. A process for the preparation of a compound of formula I

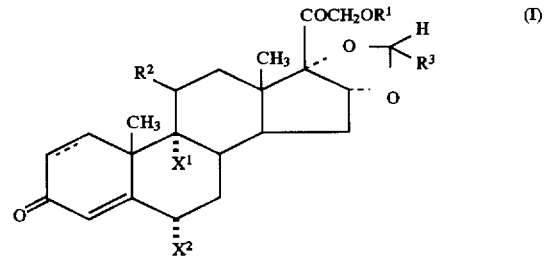

or a stereoisomer thereof, wherein:

the 1,2-position is saturated or is a double bond;

$X^1$ and $X^2$ are each independently hydrogen or halogen;

$R^1$ is hydrogen or acyl;

$R^2$ is hydroxyl, acyloxy or oxo; and $R^3$ is alkyl, comprising
reacting a compound of formula (II)

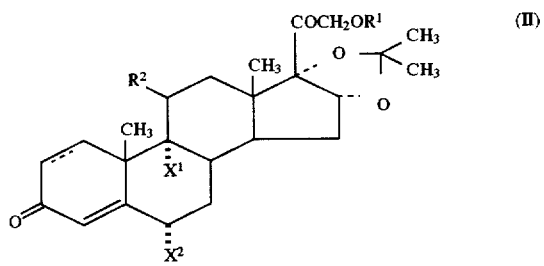
(II)

wherein the 1,2 position is saturated or is a double bond and $X^1$, $X^2$, $R^1$ and $R^2$ are as defined above, with an aldehyde $R^3CHO$, wherein $R^3$ is as defined above, in phosphoric acid or about 60% to about 75% w/w sulphuric acid.

2. A process according to claim 1, wherein $R^1$ is hydrogen and $R^2$ is hydroxyl.

3. A process according to claim 1 wherein $X^1$ and $X^2$ are both fluorine atoms.

4. process according to claim 1 in which $R^3$ is n-propyl.

5. A process according to claim 1, wherein the resulting compound has the formula III

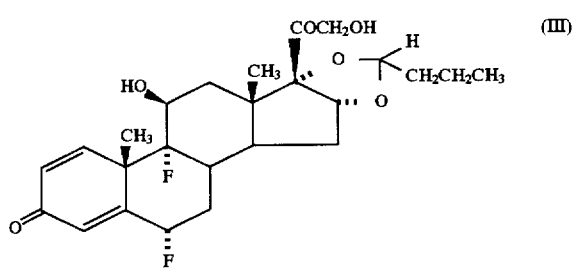
(III)

or a stereoisomer thereof.

6. A process according to claim 1, wherein formula I is (22R)- 16α,17α-butylidenedioxy-6α,9α difluoro-11β, 21-dihyldroxypregna-1,4-diene-3,20-dione.

7. A process according to claim 1 in which the reaction is effected using about 60% to about 75% w/w sulphuric acid.

8. A process according to claim 7 using about 60% to about 65% w/w sulphuric acid.

9. A process according to claim 1 in which the reaction is effected using phosphoric acid.

10. A process according to claim 9 using about 85% phosphoric acid.

11. A process according to claim 1 in which the reaction is effected at a temperature of about 0° C. to about 50° C.

12. A process according to claim 1, followed by treatment of the resulting compound of formula (I) with a catalytic amount of perchloric acid to provide an improved percentage of the 22R-isomer of formula (I).

13. A process according to claim 2, wherein $X^1$ and $X^2$ are both fluorine atoms.

14. A process according to claim 2 in which $R^3$ is n-propyl.

15. A process according to claim 3 in which $R^3$ is n-propyl.

16. A process according to claim 2 in which the reaction is effected using about 60% to about 75% w/w sulphuric acid.

17. A process according to claim 3 in which the reaction is effected using about 60% to about 75% w/w sulphuric acid.

18. A process according to claim 4 in which the reaction is effected using about 60% to about 75% w/w sulphuric acid.

19. A process according to claim 5 in which the reaction is effected using about 60% to about 75% w/w sulphuric acid.

20. A process according to claim 3 in which the reaction is effected using phosphoric acid.

21. A process according to claim 4 in which the reaction is effected using phosphoric acid.

22. A process according to claim 3 in which the reaction is effected at a temperature of about 0° C. to about 50° C.

23. A process according to claim 7 in which the reaction is effected at a temperature of about 0° C. to about 50° C.

24. A process according to claim 9 in which the reaction is effected at a temperature of about 0° C. to about 50° C.

25. A process according to claim 3, followed by treatment of the resulting compound of formula (I) with a catalytic amount of perchloric acid to provide an improved percentage of the 22R-isomer of formula (I).

26. A process according to claim 7, followed by treatment of the resulting compound of formula (I) with a catalytic amount of perchloric acid to provide an improved percentage of the 22R-isomer of formula (I).

27. A process according to claim 9, followed by treatment of the resulting compound of formula (I) with a catalytic amount of perchloric acid to provide an improved percentage of the 22R-isomer of formula (I).

* * * * *